US006203782B1

United States Patent
Eliaz et al.

(10) Patent No.: US 6,203,782 B1
(45) Date of Patent: *Mar. 20, 2001

(54) METHOD AND PRODUCT FOR PROMOTING HAIR GROWTH AND TREATING SKIN CONDITIONS

(75) Inventors: Isaac G. Eliaz, San Rafael, CA (US); Shmuel Gonen, Kiryat Ono (IL)

(73) Assignee: Universal Biologics, Inc., San Rafael, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/645,767

(22) Filed: May 14, 1996

Related U.S. Application Data

(63) Continuation-in-part of application No. 08/416,246, filed on Apr. 4, 1995, now abandoned, which is a continuation of application No. 08/106,804, filed on Aug. 16, 1993, now Pat. No. 5,422,100, which is a continuation of application No. 07/659,959, filed on Feb. 25, 1991, now abandoned, which is a continuation-in-part of application No. 07/487,886, filed on Mar. 2, 1990, now abandoned.

(51) Int. Cl.[7] ..................................................... A61K 7/06
(52) U.S. Cl. ..................... 424/70.1; 514/880; 514/852; 424/74
(58) Field of Search ............... 424/70.1, 74, 78.02, 424/195.1; 514/852, 861, 863, 864, 880, 881

(56) References Cited

U.S. PATENT DOCUMENTS

| 4,048,301 | 9/1977 | Papantoniou ........................... 424/70 |
| 5,422,100 | * 6/1995 | Eliaz et al. ........................ 424/70.11 |

FOREIGN PATENT DOCUMENTS

| 177 920 | 4/1986 | (EP) . |
| 308 210 | 3/1989 | (EP) . |
| 2 424 024 | 11/1979 | (FR) . |
| 2 557 797 | 7/1985 | (FR) . |
| 2 671 721 | 7/1992 | (FR) . |
| 60-146829 | 8/1985 | (JP) . |
| 2 048 514 | 2/1990 | (JP) . |
| 3 176 413 | 7/1991 | (JP) . |

OTHER PUBLICATIONS

WPIDS abstract, AN 90–096011 [13], (JP 02048514 A), Feb. 1990.*
WPIDS abstract, AN: 80–11414 c [07], Moreno, M. (FR 2424024), Dec. 28, 1979.*
Susan Budavari, "The Merck Index", Merck & Co., Inc. 1989, pp. 102, 107, 622.
Hertel, Hermann, Seifen–Ole–Fette–Wachse, 107:313–314 (Jul. 1981).
Weiss, R. F., Arztezeitschrift fur Naturheilverfahren, 4:225–228 (Apr. 1982).
Chemical Abstracts, 112(13):115600u (1989).
Chemical Abstracts, 112(14):125228t (1989).
Chemical Abstracts, 115(6):57180f (1990).

* cited by examiner

*Primary Examiner*—Theodore J. Criares
(74) *Attorney, Agent, or Firm*—Piper Marbury Rudnick & Wolfe, LLP; Steven B. Kelber

(57) ABSTRACT

Methods and compositions for promoting hair growth, preventing or minimizing hair loss, enhancing or restoring hair color or remelanization and treating other hair and skin conditions are disclosed. The methods include topical application of the compositions to the skin or hair follicles being treated. The compositions include as an essential component a treatment agent in an amount effective for treating the condition and selected from the class of compounds consisting of anole, anethole, analogs thereof, polymers thereof and mixtures thereof. Various combinations of these compounds may be found in herb families including umbelliferae, magnoliaceae, labiatae and rutaceae. The invention preferably contemplates selecting the treatment agent from the class of herbs consisting of *Foeniculum vulgares* (fennel seed), *Pimpinella anisum* (anise), *Carum carvi* (caraway seeds) and mixtures thereof with each other and/or other herbs.

9 Claims, 2 Drawing Sheets

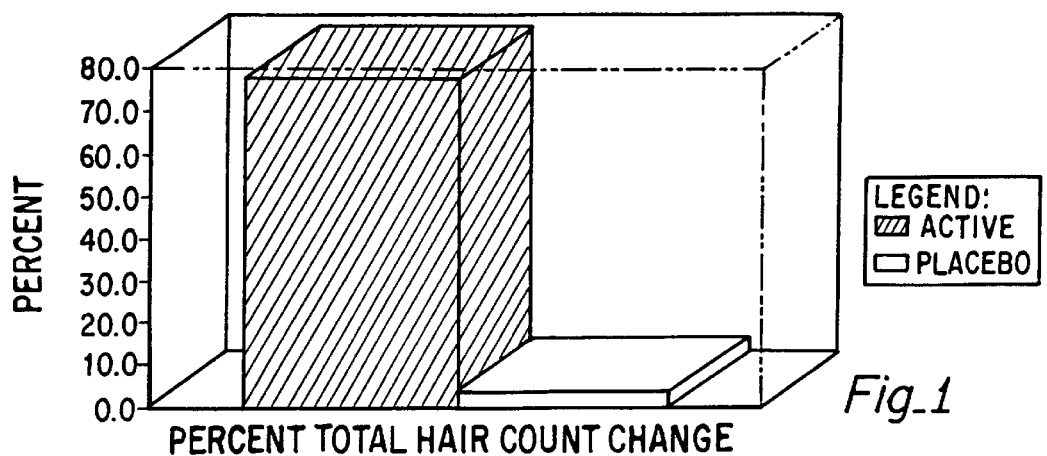
Fig_1
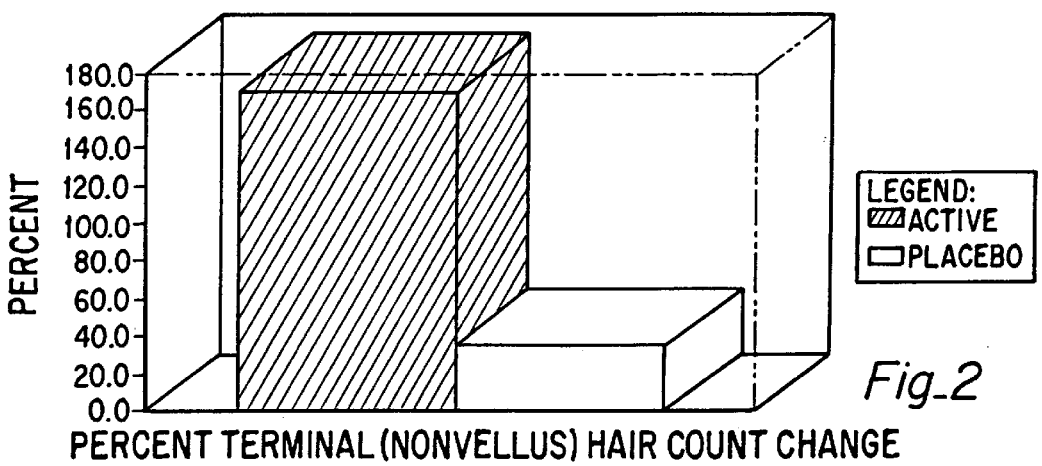
Fig_2
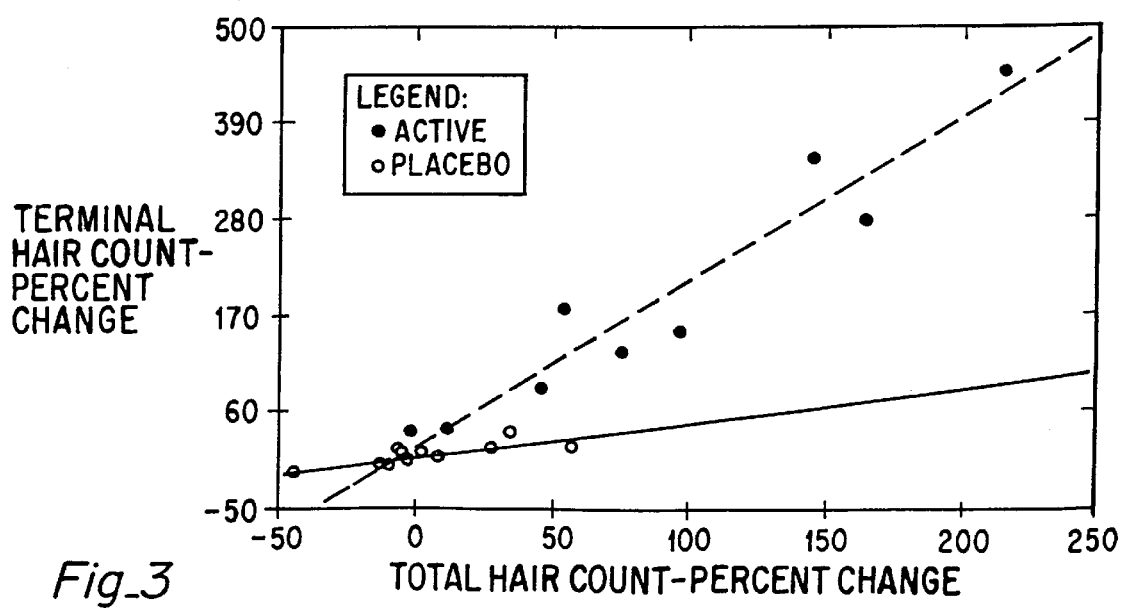
Fig_3

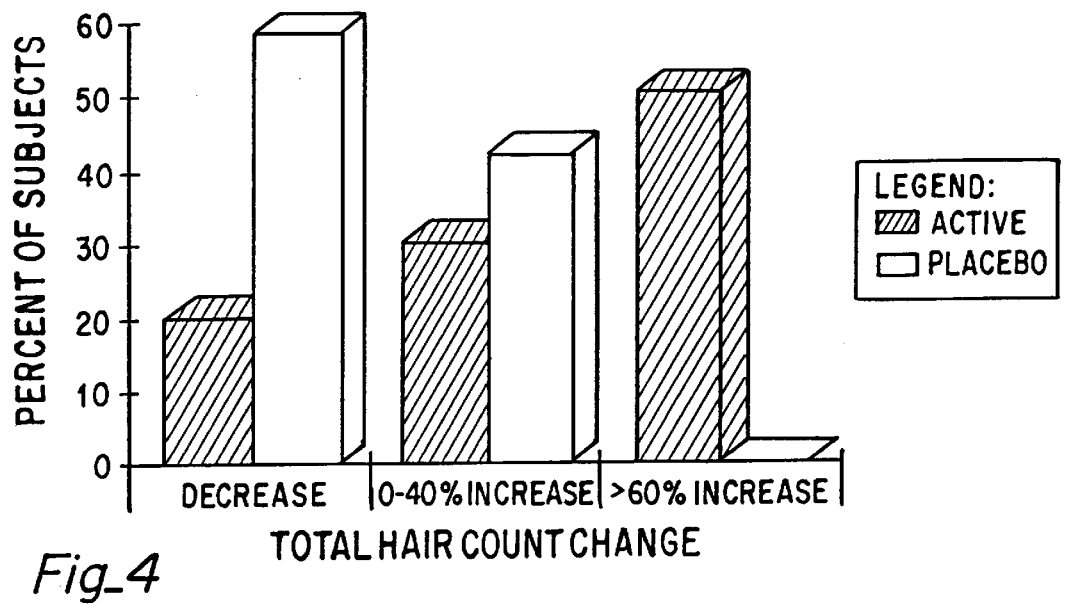
Fig_4
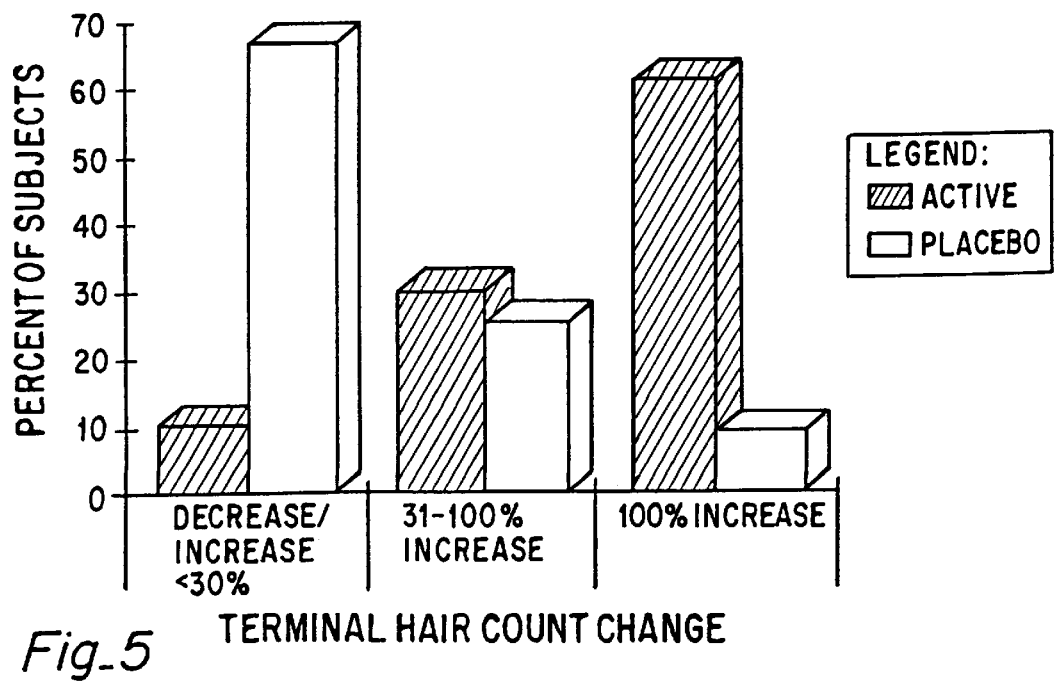
Fig_5

METHOD AND PRODUCT FOR PROMOTING HAIR GROWTH AND TREATING SKIN CONDITIONS

RELATED APPLICATIONS

This is a continuation-in-part of application Ser. No. 08/416,246, filed Apr. 4, 1995, now abandoned, which is a continuation of application Ser. No. 08/106,804, filed Aug. 16, 1993, now U.S. Pat. No. 5,422,100, issued Jun. 6, 1995, which is a continuation of application Ser. No. 07/659,959, filed Feb. 25, 1991, now abandoned, which is a continuation-in-part of application Ser. No. 07/487,886, filed Mar. 2, 1990, which is now abandoned. These applications and patent are incorporated herein by reference in their entirety.

BACKGROUND OF THE INVENTION

1. Field of the Invention

The present intention relates to methods and products for treating hair and skin conditions. Hair treatments include promoting hair growth in general and, in particular, promoting growth of hair transplants, preventing, stopping or minimizing hair loss, reducing and/or preventing hair fallout during chemotherapy, conditioning the hair and scalp, thickening the hair, eyebrows and eyelashes, treating dandruff, etc. Treatments for skin conditions include smoothing of the skin, treating seborrheic dermatitis, treating cuticles, nails, and nail fungus, treating psoriasis, healing of wounds in the skin, etc.

2. Discussion of the Background

Treatments for hair loss and other scalp and hair disorders addressed by the invention have long been sought, and many treatments utilizing compositions based on extracts from naturally-occurring herbs have been proposed. However, conclusive evidence of the efficacy of known compositions has been hard to find, and many of the reported or suggested results achieved with the prior art compositions lack scientific credibility.

The present inventors, however, have discovered a composition which has been conclusively demonstrated to produce a significant improvement in the conditions for which it is used as a treatment. Most unexpectedly, the composition has been found to be effective for treating hair loss in women, as well as in men. The present inventors have conducted scientific studies demonstrating the effectiveness of the composition of the invention.

A number of treatment agents are disclosed in U.S. Pat. No. 4,874,791 which describes a hair-growing agent containing as an effective ingredient an aliphatic carboxylic acid having an odd number of carbon atoms or a derivative thereof.

U.S. Pat. No. 4,814,351 discloses yet another scalp treatment for reducing average daily hair loss by periodically applying to the scalp a composition containing an active chelating agent. The background discussion of this reference sets forth various theories for enhancement or restoration of hair color to its natural or pre-gray color or, in other words, remelanization of the hair.

U.S. Pat. No. 4,769,231 discloses a hair tonic composition containing an extract from dong chong xia cao.

U.S. Pat. No. 4,853,216 discloses a topical composition containing an alpha adrenergic agonist using a pilomotor effect to enhance shaving.

Still other references disclose active agents for treating various skin conditions. U.S. Pat. No. 4,719,226 discloses a percutaneous absorption preparation and a process for preparing the product. U.S. Pat. No. 4,725,609 discloses a topical nicotinamide composition for promoting angiogenesis, re-epithelialization and wound healing. U.S. Pat. No. 4,656,192 discloses tropolone esters as antimicrobial agents, hair growth stimulants and dental medicines.

JP-2048514 discloses a hair-growth promoting agent which contains a crude extract, an anionic surfactant and a surfactant having nitrogen, and not being an anionic surfactant.

JP-60-146829 discloses a testosterone 5-α-reductase inhibitor for use as an anti-androgen. The disclosed compositions contain an extract of a herb selected from a list of 26 ingredients, together with a solvent. The composition is disclosed as a cosmetic for use as a hair tonic or skin care.

The Kosmetika Aerosole Riechstoffe discloses a variety of uses of herbal products. Fennel is mentioned for use in mouth and eye care and in bathing preparations. Hops, camomile, rosemary and yarrow are mentioned as having applications including hair or scalp care, or shampoos.

FR-2424024 discloses a composition for inhibiting hair loss using a lotion of artemesia, parsley and 36-hour fermented grapes brewed in a particular fashion requiring maceration prior to filtration. Fennel and orange flower may be added to the mixing pot as optional ingredients.

In addition, various herbs have long been known in chinese herbology or medicine as having various medicinal or physiological applications. Various herbs have been discussed as being effective for controlling the quality and color of hair as well being effective hair growth agents. In this connection, different herbs have been disclosed for treating pre-mature graying of hair. These herbs include:

1. He shou wu—Radix polygoni multiform;

2. Hei zhi ma—Semen sesami indici; and

3. Gou gi zi—Fructus lycii chinensis.

These herbs were used particularly in oral applications such as in teas, but were sometimes employed as local external or topical applications.

The following herbs have also been considered suitable for treating baldness in local or topical applications:

1. Gu sui bu—Rhizoma gusuibu (drynaria);

2. Ce bai ye—Cacumen biotae orientalis.

Ce bai ye, according to Chinese literature, when made in a tincture from the fresh plant, has been tested and found to produce sprouting of hair on bald people, reportedly in at least thirteen cases. (Chinese Herbal Medicine, Material Medica—Bensky Gamble, page 370.)

Prior art attempts to produce a hair growth promotor have investigated a large number of compounds as candidates but have generally considered factors such as a particular mixture of surfactants or a specific process to be essential. The near-alchemical requirements of the prior art for special process features and the long lists of potential ingredients, coupled with failure to provide conclusive scientifically proven results clearly indicates that prior art compositions and methods are problematic and do not provide the desired results. Notwithstanding significant efforts to develop compositions which promote hair growth, a need continues to exist for compositions and methods with provable results.

Further, new problems associated with hair growth have arisen as a result of the advent of new medical techniques. For example, surgical hair transplants are now well known. However, hair transplant grafts often fall out after about 2–4 weeks. Although most grafts grow back after 3–4 months, additional transplant surgery may be needed. A need exists, therefore, for a specific treatment of hair transplant patients by conditioning the scalp, preventing or reducing hair fall out, promoting fast healing of the surgical sites and the prevention and shortening of hair shock time.

The widespread use of chemotherapy to treat cancers is also well known. However, conventional chemotherapy often results in hair fall out during chemotherapeutic treatment. Significant time is required for the lost hair to regrow producing social stigma and discomfort. A need exists for a treatment to overcome these problems with chemotherapeutic hair fall out.

Efforts to discover or develop such materials demonstrate a continuing need for compositions or materials which are effective for promoting hair growth, preventing or minimizing hair loss and for treating various skin conditions. It is of course particularly important that such materials or compositions be uniformly effective and safe to use in order to enhance their effectiveness for use by large numbers of people.

SUMMARY OF THE INVENTION

Accordingly, a need continues to exist for improved methods and products for treating hair and skin conditions including promoting new hair growth, promoting hair growth before, during or after chemotherapy, for promoting hair growth in hair transplant patients, preventing, stopping or minimizing hair fall out, conditioning the hair and scalp, thickening the hair, treating dandruff, smoothing the skin, treating seborrheic dermatitis, treating psoriasis, treating cuticles, nails, and nail fungus, healing of wounds in the skin, etc. Such a wide variety of applications is contemplated by the present invention and is to be understood as being intended by references to methods and/or products for treating hair and skin conditions.

The invention specifically contemplates the enhancement or restoration of hair color to its natural or "pre-gray" color or, in other words, remelanization of the hair. This has been found to result in a change in the hair color and enrichment of the hair color in addition to darkening the hair.

It is therefore an object of the invention to provide methods and products for treating such hair and skin conditions and also for color enhancement or restoration and remelanization of hair by topically applying to the skin or to the scalp including hair and hair follicles of a host in need thereof a treatment composition containing as an essential component a treatment agent in a treatment effective amount and including an active ingredient selected from anole, anethole, analogs thereof, polymers thereof and mixtures thereof.

Particular analogs include estragole, which is an allyl analog of anethole. Suitable anole polymers include, for example, dianole, known to have estrogenic-like activity. Dianethole and photoanethole are two polymers of anethole also having estrogenic-like activity.

Characteristics of these compounds are discussed in a number of references, for example, an article entitled "Fennel and Anise as Estrogenic Agents" by Michael Albert-Puleo, published in *Journal of Ethnopharmacoloqy*, 2 (1980) 337–344. This article is incorporated herein by reference in its entirety.

For purposes of identification, referring again to the article noted immediately above, anole is commonly known as 4-(1-propenyl)phenol and has the structure shown below;

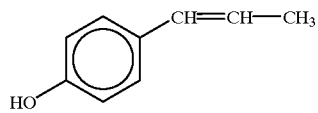

anethole is commonly known as p-propenyl anisole and has the structure shown below;

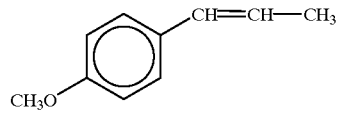

and estragole, which is an analog of anethole, is commonly known as 1-methoxy-4-(2-propyl)benzene and has the structure shown below.

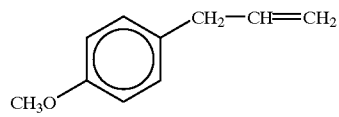

The compound fenchone has the structure shown below.

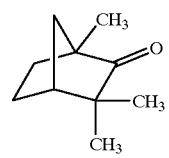

The invention contemplates mixtures of two or more of the compounds noted above, in combination with each other in the treatment composition. Such compounds have been found to be particularly effective for synergistically enhancing treatment effectiveness and to facilitate penetration of the treatment composition into the skin, nails, hair or hair follicles.

The compounds listed above may be obtained from a variety of sources. For example, the compounds and their polymers may be produced synthetically, but preferably they are obtained from various herbs having effective amounts of one or more of the compounds. Such herbs may be selected from the class of herb families consisting of umbelliferae, magnoliaceae, libiatae and rutaceae.

It is a further object of the invention to provide methods and products for treating hair and skin conditions where a treatment composition is topically applied to the skin, nails, and/or hair and hair follicles, the treatment agent including tinctures or extracts of one or more herbs selected from *Foeniculum vulgares* (fennel seed), *Pimpinella anisum* (anise), other types of anise, *Carum carvi* (caraway seeds) and mixtures thereof.

Although the present invention preferably contemplates topical application to the hair and/or skin to be treated, it is noted that such an application is generally believed necessary in order to provide an adequate concentration of the necessary compounds in the local area of hair and/or skin to be treated. However, hair and/or skin treatment by such topical application may be enhanced or supplemented by additional internal consumption of the same herbs.

It is also an object of the invention to specifically employ the treatment of the invention as summarized above and described in greater detail below to restore hair on a person in need of hair restoration, including promoting hair growth, hair thickening and/or coloring (remelanization) of the hair and/or skin conditioning.

The invention also contemplates solving the problem of treating hair transplants in hair transplant patients in order to condition the scalp, promote faster healing of the surgical sites, prevent or reduce hair fall out and prevent or shorten the hair shock time. This problem is satisfactorily solved by the present invention which generally promotes faster graft healing, faster growth of the hair transplants, less itching and less hair fallout as confirmed below.

The present invention also addresses the problem of hair fall out during chemotherapy. Administration of the composition of the invention before, during or after chemotherapy reduces and prevents hair fall out in patients undergoing chemotherapy.

It is a further object of the present invention to similarly treat hair, nail components including nails, nail fungus, and/or eyebrows and/or eyelashes.

It is yet a further object of the invention to provide a composition and method which can be administered to reduce and/or prevent hair fall out in persons undergoing chemotherapy, in particular cancer chemotherapy.

Preferably, the herbs are employed in the composition of the invention in various combinations with each other and/or with other herbs selected for synergistically enhancing treatment and/or delivery through the skin, hair or hair follicles.

Specifically, the present invention contemplates such methods and products wherein the treatment agent comprises a tincture or extract of *Foeniculum vulgares* (fennel seed). This single herb is believed to include the most effective combination of compounds as discussed above for treating hair and skin conditions contemplated by the present invention.

The invention also specifically contemplates methods and products wherein the treatment agent comprises a tincture or extract of *Pimpinella anisum* (anise). This herb has also been found to provide a very effective combination of compounds.

Both of the herbs discussed above, particularly fennel, are also preferably included in combination either with each other or with other herbs selected for synergistically enhancing treatment and/or delivery through the skin or hair follicles.

It is yet a further object of the invention to provide methods and products for treating hair and skin conditions including any of the combinations of compounds and/or herbs noted above where the treatment composition further includes optional amounts of a carrier, a masking agent, a gelling agent, fragrances and preservatives as desired and a tincture solvent for the treatment agent.

Of the optional components noted above, the carrier provides a medium for the treatment agent and other components of the treatment composition as well as masking a strong smell possible for certain of the treatment agents. A typical carrier is gum mastic. A masking agent may also be added for the purpose of masking strong smells as noted above and may preferably be formed from a tincture of one or more additional herbs. The gelling agent is of a type commonly employed in cosmetics and medicinal compositions for controlling the consistency or other physical characteristics of the treatment composition. The tincture solvent or a combination of different tincture solvents may be employed for forming the tinctures or extracts of the compounds and/or herbs comprising the treatment agent. A number of solvents including alcohol, etc. may be used for preparing the tinctures.

The methods and products of the present invention have been found to be surprisingly effective in the treatment of hair and skin conditions as noted above and discussed in greater detail below.

Additional objects and advantages of the invention are made apparent in the following description and examples of the invention, having reference to the drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 1 is a graphical representation of increased percent total hair count change as a result of the invention in an active group compared with a control (placebo) group; FIG. 1 shows the average increase in total hair count for the treatment product of the invention in the active group (77.4%) compared with the control (placebo) group (3.0%).

FIG. 2 is a graphical representation of percent terminal (non-vellus, mature and colored or melanized) hair count change achieved by the invention; FIG. 2 shows that the average terminal hair count for subjects treated by the treatment product of the invention increased by 169.4%, as compared to a 33.9% increase for the placebo treated subjects.

FIG. 3 is a graphical representation of total hair count change correlated to terminal hair count change for treatment with a composition of the invention and a placebo; FIG. 3 shows the correlation between the percentage change in terminal hair counts and the percentage change in total hair counts, in both the active (solid black dots) and placebo (circles) groups; the correlation coefficient for the active group was 0.954 while the correlation coefficient for the entire group was 0.947.

FIG. 4 is a graphical representation of total hair count change accomplished by the invention in an active group compared with a control (placebo) group; FIG. 4 shows the percentage change in total hair count for the active and placebo groups over the course of the study; the degree of change is divided into three categories: (1) subjects who had a decrease in total hair count; (2) subjects who had an increase in total hair count between 0 and 60%; and (3) subjects who had an increase in total hair count greater than 60%.

FIG. 5 is a graphical representation of terminal hair count change accomplished by the invention in an active group compared with a control (placebo) group; FIG. 5 shows the percentage change in terminal hair count for the active and placebo groups over the course of the study; the degree of change is divided into three categories: (1) subjects who had a decrease in terminal hair count or an increase of less than 30%; (2) subjects who had an increase in terminal hair count between 31% and 100%; and (3) subjects who had an increase in terminal hair count greater than 100%.

DETAILED DESCRIPTION OF THE PREFERRED EMBODIMENTS

The method and products of the invention are useful for treating conditions of keratinous structures, that is, body structures composed of keratin, an extremely tough protein substance in the hair, nails, and horny tissues of the body. As used herein, the term "hair" means hair having a hair follicle including hair on the scalp, transplanted hair, eyebrows and eyelashes. The invention is not limited to improving hair growth and structure in a particular body location. The methods and products of the invention are commonly based upon the use of a treatment agent containing an active ingredient which is selected from anole, anethole, fenchone, analogs thereof, polymers thereof and mixtures thereof, either alone or in combination with each other and additional compounds.

Of the above compounds, fenchone alone is present in a Chinese herb, Ce bai ye, which has been known to be suitable for topical application to promote hair growth. It has also been known to employ this Chinese herb for treating other skin conditions such as minor burns. However, the effectiveness of this Chinese herb for treating such conditions was not previously known to be associated with its fenchone component. In addition, neither the above Chinese herb nor other hair growth agents have been found to produce the synergistic results achieved by the compositions of the invention.

Useful combinations of the above compounds have also been found to be present in a selected class of herb families consisting of umbelliferae, magnoliaceae, labiatae and rutaceae.

The above herb families each include large numbers of herbs, only some of which have known uses. These herb families are discussed and outlined in a number of references. For example, the umbellifeae family is discussed at length in an article entitled "The Biology and Chemistry of the Umbelliferae" edited by V. H. Heywood, Dept. of Botany, univ. of Redding, England. Representative members of the above herb families are also set forth, for example, in a publication by Shui Ying Hu entitled "An enumeration of Chinese Materia Medica" and published by the Chinese University of Hong Kong, 1980.

Members of the above herb families are only of interest to the extent that they are suitable for human use. It is believed to be more important in connection with the theory of the present invention that the herbs be selected to include one or more of the compounds discussed above.

Within the above herb families, treatment agents formed as tinctures or extracts of certain herbs particularly including *Foeniculum vulqares* (fennel seed) and also *Pimpinella anisum* (anise), *Carum carvi* (caraway seeds) and mixtures thereof have been found to be particularly effective in the present invention. Of those herbs, primarily *Foeniculum vulqares* and *Pimpinella anisum* have been found to be most effective alone or preferably in combination with each other or with other herbs such as *Carum carvi* for synergistically enhancing treatment and/or delivery through the skin or hair follicles.

The discovery of the present invention is based, at least in part, upon a theory that compounds and/or herbs containing these compounds, having local estrogenic-like effects capable of counteracting testosterone in the hair follicles, would be particularly effective for promoting hair growth and/or for preventing, stopping or minimizing hair loss and/or for enhancing or restoring hair color or remelanization. The theory is based, at least partly, upon testosterone and like hormones being known causative factors for hair loss and/or male pattern baldness. This theory may also be extended to other hair and skin conditions as summarized above.

The above theory is set forth partly by way of explanation of the invention and partly to explain the contemplated advantages for the class of compounds set forth above in treating hair and skin conditions discussed herein. However, since the specific mechanism by which the compounds and/or herbs of the present invention are effective for treating such hair and skin conditions is not precisely known, the above theory is not intended to be limiting in terms of the invention.

Quite surprisingly, the composition and method of the present invention are effective in promoting general growth and health of keratinous structures in both men and women. The effective treatment of women is particularly surprising in view of the proposed theory noted above which is based, at least partly, upon estrogenic-like compounds counteracting testosterone in the hair follicles. Nevertheless, the compositions of the invention have been found to cause reversal of hair fall out and to stimulate hair growth in women.

In connection with the theory set forth above, an extract or tincture of fennel seeds was first tested because that herb is known in western herbology for promoting lactation in mothers. At the same time, fennel seeds were found to contain all of the class of compounds set forth above as well as fenchone in a significant amount. Anole and anethole, in particular, are major components of the volatile oil of fennel seeds. Similarly, anise includes anole and anethole, but is much less active physiologically than fennel. This may be due to anise containing a lower amount of certain other compounds. Caraway seeds are also from the umbelliferae herb family and are also known to promote lactation. These three herbs, especially fennel seeds, have been found to be most effective either alone or in combination with each other and/or other herbs for synergistically enhancing treatment effectiveness and for facilitating penetration of the treatment composition into the skin, nails, hair or hair follicles.

A different theory is contemplated in connection with the invention for the treatment of eyebrows and eyelashes. The hair growth mechanism for eyebrows and eyelashes, although not entirely known, is totally different from that of scalp hair and beard hair. For example, although the scalp hair and beard grow freely, eyebrows and eyelashes tend to have a limited length, even over time.

The hormonal effect which produces baldness does not apply to the eyebrows and eyelashes. Dihydrotestosterone which causes androgenic alopecia (baldness) is not the cause for loss of eyebrows and eyelashes. This is why loss of eyebrows and/or eyelashes is not more common in men. Loss of eyebrows and eyelashes can be due to mechanical damage (plucking) and different pathologies (hypo- and hyperthyroidism) and for other reasons.

Similarly, the hair fall out experienced by patients undergoing chemotherapy appears to have a different pathology which is unrelated to the hormonal effect which produces androgenic alopecia.

Notwithstanding the different pathology of hair fall out/loss suffered by patients undergoing chemotherapy, the compositions of the present invention have been demonstrated to be effective in reversing or preventing hair fall out during chemotherapy with chemotherapeutic drugs. Various classes of chemotherapeutic agents are well known for use in chemotherapy. Most of these drugs will cause hair fall out. Although this effect is temporary, it is very traumatic, especially for women. The compositions of the invention may be used to reduce or prevent hair fall out in a patient (host) undergoing chemotherapeutic treatment, for example, with an anti-neoplastic agent which causes hair fall out. Chemotherapy with known cytotoxic agents such as doxorubicin and the hydrochloride thereof, carmustine, lomustine, cytarabine, cyclophosphoramide, estramustine phosphate sodium, altretamine, hydroxyurea, ifosfamide, interferon-α-2b, procarbazine hydrochloride, mitomycin, busulfan, mitoxantrone, carboplatin, cisplatin, taxol, teniposide, streptozocin, 5-fluorouracil, methotrexate, thioguanine, mercatopurine, plicamycin, fludarabine phosphate, etc., or combinations thereof may be treated with the composition of the present invention. The composition of the present invention may be administered before, during or after chemotherapy with these known chemotherapeutic agents when administered in known doses and dosage regimes resulting in hair fall out.

It is believed that the compositions of the present invention contain what are termed "healthy growth factors" that affect different structures of the skin, scalp, hair and nails. The present invention has a general supportive and positive effect on skin in general and on keratinous substances specifically.

Table I shows amounts of the four compounds discussed above in a variety of different herbs. Thus, in accordance with the preceding description, Table I indicates a possible order of preference for certain herbs. In particular, note the heavy concentration of the first and second compounds in the two preferred herbs, *Foeniculum vulgares* and *Pimpinella anisum*.

TABLE I

| | A<br>Anole<br>(and polymers) | B<br>Anethole | C<br>Fenchone | D<br>Estragole |
|---|---|---|---|---|
| (Umbelliferae)<br>*Foeniculum vulgares* | +++ | +++ | + | + |
| (Umbelliferae)<br>*Pimpinella Anisum* | +++ | +++ | | |
| (Magnoliaceae)<br>*Illicium verum* | + | + | | |
| (Magnoliaceae)<br>*Illicium anisaturn* | + | + | | |
| (Legumnosae)<br>*Wistaria floribunda* | + | + | | |
| (Labiatae)<br>*Herba Agastache* | + | + | + | |
| (Magnoliaceae)<br>*Magnolia kobus* | + | + | + | |
| (Labiatae)<br>*Ocimum santtum* | | | + | |
| (Labiatae)<br>*Ocimum basilicum* | | | + | |
| (Rutaceae)<br>*Fagara schnifolia* | | | + | |
| (Araceae)<br>*Acorus gamineus* | | | + | |
| (Burseraceae)<br>*Boswellia serrata* | | | + | |
| (Cyprpssaceae)<br>Thuja (Biotae) | | | + | |
| (Volatile oil of leaf)<br>(Magnoliaceae)<br>*Magnolia salicifolia* | | | + | |

In the present invention, the composition is topically applied to the skin, nails, scalp, hair or hair follicles to be treated. Typically, about 2–3 cubic centimeters (cc), or very approximately about 2–3 grams, of the treatment composition can be applied to the skin or scalp in test treatments. However, smaller and larger amounts are also effective and will be readily determined by the concentration of active compounds in the treatment composition.

Furthermore, the treatment composition of the invention may be made up of only a small portion of the active compounds. Generally, it is contemplated that the treatment composition in tincture form, may contain as little as 0.5% by weight or even as low as 0.2% by weight of the active compounds. More typically, the invention contemplates that the treatment composition in tincture form will contain in the range of about 1.2–50% by weight of the treatment composition, more preferably about 2–20% by weight of the treatment composition, and most preferably about 5–15% by weight, corresponding to actual tests conducted where the treatment composition contained about 7% by weight of a tincture of the active compounds. It is again noted that a treatment composition according to the present invention may include a very wide effective concentration range of the active compounds in tincture form, depending upon concentration of the tincture and the specific therapeutic goal desired.

The compositions of the present invention may also include a carrier, solvent, excipient, cosmetic base or gelling agent. Preferably, these components are hypoallergenic, more preferably, easily absorbed by the skin. Suitable carriers, solvents, excipients, cosmetic bases and gels are well known in the art. Any formulation which allows delivery of the active compounds of the present invention to the skin, hair, hair follicles, nails or other keratinous structures are suitable for use in the present invention.

Suitable solvents include alkyl esters of fatty acids, preferably $C_{1-12}$, more preferably $C_{3-10}$, alkyl esters of saturated or unsaturated fatty acids containing 8–22 carbon atoms. Particularly preferred solvents include isopropyl myristate, octyl palmitate, WIKENOL 161 (a mixture of esters), etc. Alcohols such as ethanol, propanol, isopropanol, propylene glycol, etc., as well as aqueous mixtures of these alcohols may also be used.

In a preferred embodiment, the active compounds are extracted from herbs using a solvent to form a tincture. As used herein, the term "tincture" means a solution of the active compounds in a solvent. The ratio of herb to solvent, for fennel and other herbs, can vary widely, for example, from 2:1 to as high as 1:50 or 1:75 or even 1:100.

If desired, a known gelling agent may be added to the composition of the invention. Suitable gelling agents include a synthetic high molecular weight crosslinked polymer of acrylic acid, more specifically an acrylate/$C_{10-30}$ alkyl acrylate copolymer available for example under the trade name CARBOMER 1342. Other suitable gelling agents include cellulose and cellulose derivatives such as dihydroxyethyl cellulose (tradename ULTRAGEL). Whereas the ULTRAGEL contained mostly water, the CARBOMER 1342 was used in a ratio of about 0.5–1.0 percent by weight with the remainder of the gelling agent being purified water. Preferably, the gelling agent is added as the last component of the composition in order to produce the preferred gel form for the composition.

It is emphasized that the invention contemplates a very broad spectrum, as noted above, depending upon the concentration of the tincture in the final product. For example, the tincture or extract may preferably range from a ratio of 50 parts by weight of solvent to 1 part by weight of ground fennel seed to a ratio of 1 part by weight of solvent to 2 parts by weight of ground fennel seed.

The concentration of the tincture in the final product may vary, for example, from 0.5% by weight or as low as even 0.2% by weight, when using a more concentrated tincture, to almost 100% by weight when using a more dilute tincture within the range mentioned.

Thus, the effective amounts of the active ingredients in the treatment agent are of course much smaller than the amount of the extract in the final product since only a small portion of the treatment agent in tincture form is the active ingredient. Preferably, the anole, anethole and fenchone compounds, polymers or derivatives are individually present in an amount of at least 0.001% by weight in the treatment composition of the invention.

In summary, the effective amount of the active ingredients in the final product equals the amount of the active ingredients in the tincture/extract, in the preferred broad range specified for solvent: treatment agent (ground fennel seed) equaling 50:1 to 1:2, multiplied by the percentage of the tincture in the final product (0.2% to 100% as noted elsewhere). It is further noted that, if a compound or compounds forming the active ingredients of the treatment agent are synthesized or isolated and not part of a natural herbal extract, then the range of amounts and concentrations can be even broader than discussed above.

It is specifically to be noted that the present invention essentially requires topical (or external) application of the composition to the skin or hair of a host in need thereof. Such external treatment is contemplated for use by itself. In fact, tests conducted for the invention included only such external treatment. However, internal treatment may be used but only as a supplement to external or topical treatment as defined herein. Specifically, supplemental internal treatment is optional and not necessary to the invention while internal treatment by itself is not contemplated for the invention.

As for frequency of application, it is typically contemplated that the treatment product, in the form of either a hair cream or skin cream, liquid or other form, for example, be applied from about twice a day to about twice a month to the skin area or scalp area being treated, and taken internally as well to possibly supplement or enhance external treatment. However, effective treatment is also possible with a frequency of application of, for example, from a maximum of three to four times daily or even more frequently to once a month or even less frequently.

Effective topical treatment appears to be from about once daily to once every three days with the applied composition remaining in place for at least about 15–30 minutes and preferably for a period of about 12–24 hours.

Particularly in terms of the method of treatment for the invention, it is noted that most tests conducted heretofore were in connection with promoting hair growth or preventing, stopping or minimizing hair loss while effects on enhancing color, or restoring gray hair to its original color or, in other words, remelanization, were also observed. This typically resulted in a change of hair color, darker hair color and enriched hair color. With the methods and products of the invention being employed for other purposes, particularly for treating various skin conditions, it is possible that different application amounts and rates may be desirable. In particular, it may be found that substantially different amounts, probably smaller quantities, may be desirable for treating certain skin conditions. Optimum amounts and frequencies of application can be readily determined by those having ordinary skill in this art.

The effect of the preparation on the skin, and particularly on the nails, may be enhanced by adding various vitamins and nutrients (such as biotin, panthotenic acid, vitamin E and others).

EXAMPLES

Example 1

Method of Preparation for a Treatment Composition Employed in Prior Testing

Principal testing was carried out with a treatment composition including a tincture of *Foeniculum vulgares* (fennel seed) in combination with a tincture of *Carum carvi* (caraway seeds). A preferred treatment composition of the invention is marketed under the trade name HAIRPRIME® (11.5 wt. % fennel tincture in IPM, 1.2 wt. % dispersed gum mastic in IPM, 0.6 wt. % acrylates/$C_{10-30}$ alkyl acrylates copolymer, 0.5 wt. % diazolidinyl urea, 0.1–0.5 wt. % triethanolamine, 0.25 wt. % potassium sorbate, 0.2 wt. % methyl paraben, 0.2 wt. % fragrance, 0.15 wt. % masking herbal formula in IPM, 0.1 wt. % caraway tincture in IPM, and 0.05 wt. % propylparaben, remainder purified water to 100 wt. %) available from Universal Biologics, Inc.

The primary herb, *Foeniculum vulgares*, was first ground into a powder and tinctured in isopropyl myristate (IPM), as a solvent in a ratio of about one part by weight of fennel seed powder to three parts by weight of IMP solvent.

Vegetable gum, or gum mastic, (as a preferred carrier) was dispersed separately into IPM solvent in a ratio of about ten parts by weight IPM solvent and one part by weight gum mastic.

The fennel tincture was allowed to stand for about two weeks, mixing the tincture from time to time. After two weeks, the tincture was filtered to produce a clear liquid.

The clear fennel tincture was mixed in a blender with the dispersed mastic gum in a ratio of about nine parts by weight fennel tincture and about one part by weight gum mastic solution to produce a fennel tincture solution.

A second tincture was prepared by grinding *Carum carvi* (caraway seeds) into a powder which was then tinctured in isopropyl myristate in a ratio of about one part by weight caraway seeds and about nine parts by weight of IPM solvent. This tincture was also allowed to stand for two weeks, with stirring. Thereafter, the caraway tincture was filtered to also produce a clear liquid.

About 3% by weight of the caraway tincture was then added to the clear fennel tincture solution to form a combined herb tincture solution.

About 0.5% by weight of a selected fragrance and about 1.5% by weight of a masking formula tincture, based on the clear fennel tincture, were then added to the combined herb tincture solution. The masking formula tincture was formed from eight different herbs used to produce a masking herb tincture in the same manner as described above for the fennel tincture and the caraway tincture. The eight herbs included in the masking formula tincture included *Herba drynariae, Fructus psoraleae, Polygoni multiform, Herba agastache*, Thuja, Camomile, Mentha and Hibiscus.

The above components combined as described formed the basic active product for the treatment product of the invention. The basic active product was mixed with a gelling agent in a ratio of about one part by weight of basic active product and about twelve parts by weight of gelling agent. The gelling agent consisted of one part by weight of hydroxyethylcellulose and fifty parts by weight of water with a preservative added as necessary or desired.

Of the components noted immediately above, the fragrance and masking formula tincture were selected for producing a pleasing aroma in the basic active product while masking the harsher smell of certain components such as the volatile oils from the fennel seed. The gum mastic was used for two purposes. Initially, it helps to mask the strong smell of fennel volatile oils. In addition, the gum mastic serves as a good carrier with a capability for penetrating into the skin and/or hair follicles. The gelling agent is used in a manner common for cosmetics and other medicinal preparations to control the consistency and other physical characteristics of the product. Thus, the final concentration of components, with broad ranges in parentheses (by weight), in the resulting treatment product include:

| | | |
|---|---|---|
| 1. | Fennel tincture in IPM - 7.5% | (0.2 to nearly 100%) |
| 2. | Dispersed gum mastic in IPM - 0.8% | (0.02–10%) |
| 3. | Caraway tincture in IPM - 0.25% | (0.025–30%) |
| 4. | Masking formula in IPM - 0.15% | (0.05–25%) |
| 5. | Fragrance - 0.20% | (varied as necessary) |
| 6. | Preservative - 0.1% | (varied as necessary) |
| 7. | ULTRAGEL - as necessary | (q.s 100%, balance) |
| | Total - 100% by weight | |

Test results from a treatment composition formed according to the invention as described above are set forth below.

Test Results

1. Hair loss was halted within 2–6 weeks. Nearly 100% of the participants who complained of prior hair loss reported that hair loss stopped.

2. After four months of treatment, in over 80% of the subjects, initiation of follicle hair growth was observed. Even in those few who did not report hair growth but who continued the treatment, initiation of hair growth was observed after about six months. After one year of treatment in both men and women, in generally all states of baldness, new hair growth was observed in over ninety percent of the test subjects. These results were based upon tests with a group of about 10 men and women.

3. Female participants observed approximately 50–60% initiation of follicle hair growth.

4. It was generally noted that almost all participants in tests of the invention reported improvement in hair quality, thickness and health.

5. The participants also commonly reported a substantial decrease in dandruff. Similarly, those participants with seborrheic dermatitis also reported very significant improvement. Tests for psoriatic lesions in a few patients having those conditions also showed significant improvement. Excellent therapeutic results were noted for treatment according to the present invention in all scalp and skin ailments including but not limited to itching, dandruff, seborrheic dermatitis and psoriasis of the scalp.

6. Continued testing according to Example 1 and other examples of the present invention having indicated that use of the present invention, particularly in men over a period of about six months has achieved nearly a 100% response in reported hair growth and termination of hair loss.

7. During observation of results from tests as described above, a dramatic effect was also noted in the restoration of original hair color to gray or white hair. In this context, original hair color refers to the color of the hair before turning white. Accordingly, this effect of the invention is also referred to herein as remelanization of the hair. Thus, new hair growth and hair replaced as a part of the natural hair growth cycle according to the invention tended to restore melanin in the hair, or to achieve remelanization in the hair as noted above, so that those test subjects with graying hair were observed to have noticeably darkened hair, that is, hair approaching the original color before turning gray or an enhanced or changed color. This effect of color restoration or remelanization in the hair was noted in the vast majority of the test subjects with graying hair, nearly 100%.

Example 2

More specific test procedures were carried out with thirty individuals, both men and women, ranging in age from about 23 to about 80. These test subjects employed the treatment product of the invention prepared in accordance with Example 1 for periods of time ranging from as little as six days to as long as approximately six months.

The test subjects, at initiation of testing, had a variety of hair conditions ranging from substantially bald through receding hairlines to thinning hair and full heads of hair with varying degrees of hair falling out. Of approximately fifteen test subjects employing the treatment product of the invention for more than two months, only one test subject experienced no substantial change.

The other fourteen test subjects experienced varying degrees of success ranging from substantial new hair growth to hair loss being controlled at a normal rate for individuals with generally healthy heads of hair. Of the fifteen test subjects employing the treatment product of the invention for less than two months, six subjects experienced no change. Of those six subjects, three had employed the treatment product for less than two weeks. The remainder of the fifteen test subjects using the treatment product for less than two months also experienced varying degrees of success ranging from new hair growth to loss of hair being in a normal range.

The results of Examples 1 and 2 demonstrate the efficacy and effectiveness of the treatment product of Example 1.

Example 3

Based upon theory, study of test results as set forth above and other factors, it is contemplated that a range of treatment products can be produced employing different active ingredients selected as noted above from the various compounds and/or herbs to produce similar results as in Examples 1 and 2. However, those results may not be as substantial in view of the preferred herb being employed in the treatment product of Example 1. It is contemplated that the other herbs and/or compounds of the present invention as described above will produce similarly effective treatment compositions.

Example 4

The various treatment products as generally discussed in Example 3 are topically applied in the same manner noted above. In all of the examples, internal consumption may enhance treatment when combined with topical application. In particular, similar topical application is contemplated for various hair and skin conditions. In each such application, the treatment composition is topically applied to the area with the particular affliction.

In Examples 2–4, a dramatic result of the invention was observed in terms of substantial restoration of hair color to the hair color of the subject prior to the hair becoming gray or enhanced, changed or darker color or in other words, remelanization in the hair. The results accomplished by the various treatment products described above and particularly in Examples 1–4 are described below with reference to a double-blind placebo controlled study using proven state-of-the-art technology.

The study set forth below particularly illustrates the effectiveness of the invention from a double-blind study performed with suitable controls.

Example 5

Double Blind Clinical Trial for Androgenetic Alopecia: Topical Treatment With The Treatment Product of the Invention A Standardized 7.5% Herbal Extract Preparation Twenty-four healthy male subjects with Stable III–IV androgenetic alopecia were enrolled in a randomized, double-blind, parallel vehicle-controlled study to confirm the effectiveness and safety of a topically applied, standardized herbal preparation (the treatment product of the invention) cream 7.5 wt. % used once daily in the treatment of androgenetic alopecia.

Androgenetic alopecia is the most common cause of hair loss affecting one third of both men and women. In preliminary studies, the treatment product of the invention, a standardized herbal extract in a vehicle, produced encouraging results as a hair growth agent. In one pilot study, all 18 subjects showed increased hair counts, averaging 119%. A very high percentage (50–100%) of conversion from vellus to terminal hair, and hair remelanization (50–100%) was observed.

Materials and Method

Study Design and Medications

The treatment product of the invention is a standardized 7.5 wt. % herbal extract in a cream base vehicle. The extract is standardized by replicative methods, including standardization against specific compounds which appear naturally in the extract.

A double-blind, placebo-controlled trial was conducted to compare the effect of the treatment product of the invention on hair growth in males with androgenetic alopecia against its placebo vehicle. Patients applied the cream to the scalp daily, at approximately 24 hour intervals, for 40 weeks and were seen in the clinic for efficacy and evaluation every 4 weeks throughout the study.

Twenty-four healthy male subjects under the age of 55 were selected for the study. The average age of the participants in the active group was 45.6 years versus 40.5 years for the placebo group. All subjects had State III–IV androgenetic alopecia. Eight subjects had excessive hair loss. The initial evaluation included health history, physical exam and evaluation of the alopecia condition. Any subjects with underlying diseases or subjects using systemic drugs (e.g., steroids, anti-hypertensives, cytotoxic compounds, vasodilators, anti-convulsant drugs, beta blockers, spironolactone, cimetidine, cyclosporine, anti-depressants) were excluded from the study. Each subject was tattooed with a permanent ink on their vertex area, creating a one centimeter triangle. The hair in the triangle was collected and the subjects entered an 8 week baseline period evaluation before beginning treatment.

Using a randomized, double-blind protocol, the subjects were given either the treatment product of the invention or a placebo of vehicle only. Both the active and the placebo groups were each randomly assigned four subjects with excessive hair loss. Subjects washed their hair daily with shampoo and applied the treatment product of the invention cream to the scalp daily, leaving the cream on for twenty-four hours. Subjects were followed every four weeks and had their hair collected six times at eight week intervals (eight weeks at baseline and an additional forty weeks of follow-up).

Assessment Procedures

Two the commonly used methods of evaluating hair growth are:

(1) counting the hair on the scalp in a marked area and (2) various photographic techniques. Both methods can have a large margin of error due to the difficulty in counting hair on the scalp and the possibility of photographing a bent hair shaft and counting it as two hairs. To avoid these problems a more accurate method for evaluating hair growth was employed, based on a protocol developed by Price (Dermatol., 95:683–687, 1990). The hair growth evaluation included: total hair count, terminal (non-vellus, melanized, mature) hair count, hair length, and total hair weight.

Each subject was tattooed with permanent ink at three points on their vertex area creating a one centimeter triangle. After rinsing the hair of the permanent site with water and soap, the hair was washed with acetone to remove any debris that could change its weight. The hair from the triangle was collected using great care to harvest only within the marked area.

The hair collected was placed on white paper, counted and then divided into terminal hair and vellus hair. The terminal hairs were then counted. The ten randomly selected hairs were also measured for length as part of the evaluation.

The total weight of all the hair samples collected were measured on an analytical scale using the same paper, on the same day, to avoid variations in temperature and humidity.

Results

Efficacy results demonstrate that the treatment product of the invention cream, used once daily, is more effective than the placebo cream vehicle in the treatment of androgenetic alopecia. The initial and final measurements of the active and placebo groups are presented in Table II and Table III below. Table IV compares the average percentage change from baseline of the total hair count, terminal hair count, total hair weight, and average hair length of the ten sample hairs, between the group treated with the product of the invention and the placebo-treated group.

After 40 weeks, 70% of the subjects in the active group had greater than a 30% increase in total hair count, compared with 16% of the subjects in the placebo group. The average total hair count for the group treated with the composition of the invention increased by 77.4%, compared to a 3% increase for the placebo treated subjects (average p value=0.005) (FIG. 1). 90% of the subjects in the active group had greater than a 30% increase in terminal hair counts, compared with 33% of the subjects in the placebo group. The average terminal hair count for the group treated with the composition of the invention increased by 169.4% over the same period, as compared to a 33.9% increase for the placebo treated group (average p=0.001) (FIG. 2). The average total hair weight of the active group increased by 49.3% compared to a 20.5% increase for the placebo group (p value=0.16). All the subjects in the active group had increased total hair weight, whereas 41.6% of the subjects in the placebo group had decreased total hair weight. The average hair length change for the 10 randomly selected hairs was 29.8% for the active group and 21.7% for the placebo (p=0.50).

No local irritation, sensitization or other adverse effects were observed or reported in either the active or placebo groups.

TABLE II

ACTIVE GROUP

| Subject | AA1 | AA2 | AA8 | AA11 | BB1 | BB2 | BB3 | BB7 | BB8 | BB13 |
|---|---|---|---|---|---|---|---|---|---|---|
| Initial Measurements | | | | | | | | | | |
| Total Hair Count | 51 | 84 | 29 | 7 | 86 | 63 | 5 | 47 | 75 | 23 |
| Terminal Hair Count | 32 | 34 | 18 | 2 | 33 | 42 | 4 | 28 | 48 | 8 |
| Hair length-cm (8 Weeks) | 1.3 | 1.6 | 1.28 | 0.29 | 1.72 | 1.72 | 1.6 | 1.12 | 1.91 | 1.51 |
| Hair Weight-gm (8 wks) | .001 | .0022 | .0011 | .00029 | .0016 | .00185 | | .0021 | 0.0032 | .00137 |
| Final Measurements | | | | | | | | | | |
| Total Hair Count | 89 | 128 | 76 | 17 | 84 | 70 | 4 | 92 | 108 | 72 |
| Terminal Hair Count | 73 | 94 | 68 | 9 | 46 | 58 | 4 | 70 | 89 | 44 |
| Hair Length-cm (8 wks) | 1.98 | 1.66 | 1.82 | 0.45 | 1.92 | 2.49 | 1.51 | 1.76 | 2.71 | 1.44 |
| Hair Weight-gm (8 wks) | .0016 | .00232 | .00258 | .004 | .0018 | .0035 | | .00267 | .00489 | .0017 |
| Results | | | | | | | | | | |
| Total Hair Count Change | 38 | 44 | 47 | 10 | -2 | 7 | -1 | 45 | 33 | 49 |
| % Total Hair Count Change | 75% | 52% | 162% | 143% | -2% | 11% | -20% | 96% | 44% | 213% |
| Terminal Hair Count Change | 41 | 60 | 50 | 7 | 13 | 16 | 0 | 42 | 41 | 36 |
| % Terminal Hair Count Change | 128% | 176% | 278% | 350% | 39% | 38% | 0% | 150% | .85% | 450% |
| Hair Length Change-cm | .68 | .06 | 0.54 | .16 | 0.2 | .77 | -0.09 | .64 | .8 | -0.07 |
| % Hair Length Change | 52% | 4% | 42% | 55% | 12% | 45% | -6% | 57% | 42% | -5% |
| Hair Weight Change-gm | .0006 | .00012 | .00148 | .00011 | .0002 | .00165 | 0 | .00057 | .00169 | .00033 |
| % Hair Weight Change | 60% | 5% | 135% | 38% | 13% | 89% | | 27% | 53% | 24% |

TABLE III

PLACEBO GROUP

| Subject | AA5 | AA7 | AA12 | AA19 | BB4 | BB5 | BB6 | BB9 | BB10 | BB11 | BB12 | BB15 |
|---|---|---|---|---|---|---|---|---|---|---|---|---|
| Initial Measurements | | | | | | | | | | | | |
| Total Hair Count | 40 | 44 | 104 | 34 | 42 | 43 | 88 | 45 | 62 | 67 | 59 | 98 |
| Terminal Hair Count | 30 | 21 | 46 | 22 | 14 | 27 | 48 | 18 | 46 | 40 | 17 | 62 |
| Hair length-cm (8 wks) | 1.5 | 1.32 | 1.61 | 1.11 | 1.61 | 1.34 | 1.7 | 0.87 | 1.75 | 1.74 | 1.52 | 1.8 |
| Heir Wgt-gm (8 wks) | .001 | .0011 | .0019 | .0018 | .0013 | .0013 | .0024 | .0013 | .0025 | .003 | .0022 | .0042 |
| Final Measurements | | | | | | | | | | | | |
| Time followed (wks) | 40 | 32 | 40 | 40 | 40 | 40 | 40 | 24 | 32 | 40 | 40 | 40 |
| Total Hair Count | 36 | 56 | 112 | 33 | 66 | 24 | 118 | 39 | 64 | 61 | 58 | 92 |
| Terminal Hair Count | 30 | 38 | 54. | 24 | 34 | 18 | 86 | 18 | 57 | 36 | 29 | 78 |
| Hair Length-gm (8 wks) | 1.39 | 1.94 | 2.35 | 1.64 | 1.79 | 0.97 | 1.71 | 1.47 | 2.17 | 1.61 | 2.22 | 1.99 |
| Hair Weight-gm (8 wks) | .0006 | .0024 | .0029 | .00142 | .0021 | .00098 | .00432 | .0014 | .0031 | .0025 | .0024 | .0036 |
| Results | | | | | | | | | | | | |
| Total Hair Ct. Chg | -4 | 12 | 8 | -1 | 24 | -19 | 30 | -6 | 2 | -6 | -3 | -6 |
| % Total Hair Ct. Chg | -10% | 27% | 8% | -3% | 57% | -44% | 34% | -13% | 3% | -9% | -5% | |
| Terminal Hair Ct Chg | 0 | 17 | 8 | 2 | 20 | -9 | 38 | 0 | 11 | -4 | 12 | 16 |
| % Terminal Hair Ct Chg | 0% | 81% | 17% | 9% | 143% | -33% | 79% | 0% | 24% | -10% | 71% | 26% |
| Hair Length Change-cm | -0.11 | 0.62 | 0.74 | 0.53 | 0.18 | -0.37 | 0.01 | 0.6 | 0.42 | -0.13 | 0.7 | 0.19 |

TABLE IV

Average Percentage Change Between The Active Group and Placebo Group

| | Average % Change Active Group | Average % Change Placebo Group | T Test P Value |
|---|---|---|---|
| Total Hair Count: | 77.4% | 3.0% | 0.005 |
| Terminal Hair Count: | 169.4% | 33.9% | 0.001 |
| Total Hair Weight | 49.3% | 20.4% | 0.162 |
| Average Hair Length | 29.8% | 21.7% | 0.506 |

Table IV compares the average percentage change between the active group treated according to the invention and the placebo-treated groups for: total hair count, terminal hair count, total hair weight, and average hair length of ten sample hairs.

Comments

The data from this study clearly demonstrate that the composition cream of the invention, 7.5 wt. %, used once daily, is safe and significantly more effective than the placebo cream vehicle in the treatment of androgenetic alopecia.

The most dramatic increases were seen in total hair counts and in terminal hair counts for the subjects who received the active treatment, compared to those who received the placebo. An excellent correlation was also found between the percentage increase in total hair count and the percentage increase in terminal hair count (FIG. 3). The correlation coefficient was 0.954 for the active group and 0.947 for the entire study group (1.00 being a perfect correlation). Therefore, counting only terminal hair may be a primary quantitative estimator for hair growth.

Example 6

Eyebrow Hair Growth Study

This study was also conducted with a hair treatment product according to the preferred composition of the invention (Example 1). In a double-blind, placebo controlled study, the product was proven to stop hair loss and promote new hair growth. Clinical reports have shown the treatment product of the invention to be effective in promoting eyebrow hair growth, thickening of the eyebrows, and faster and longer eyebrow growth.

The purpose of the eyebrow study was to confirm the effects of the treatment product of the invention on thinning eyebrows.

Materials and Methods

Seven subjects (6 women and 1 man) enrolled in the study. The subjects applied the cream product of the invention to their eyebrows daily for a minimum of four months.

Evaluation

The evaluation included the following parameters:

1. Change in thinning eyebrow pattern,
2. Change in eyebrow hair growth rate and eyebrow hair length, and
3. New hair growth.

Results

All seven subjects reported that eyebrow thinning process stopped. All subjects reported that their eyebrow hair grew longer and faster requiring them to pluck their eyebrows more often. Three subjects had to pluck their eyebrows for the first time in their lives.

Five out of the seven subjects (72%) had new eyebrow hair growth at the margins of the existing eyebrows. The new hair appeared within two to four months of application.

The treatment product of the invention is effective in promoting eyebrow growth, thickening of the eyebrows, and faster and longer eyebrow growth.

Example 7

Nail Treatment Study

The purpose of the nail treatment study was to confirm the effects of the preparation on twelve (12) women with weak, brittle nails and cuticle problems. The composition of Example 1 was found to be effective in the treatment of other skin and hair components. The composition of the invention was found to be particularly effective for brittle nails and dry inflamed cuticles.

Materials and Methods

Twelve (12) female subjects ages 22 to 53 enrolled in the study. The women worked in different jobs, including typing and work in which they utilized their fingers. The subjects were evaluated before starting to use the nail preparation.

The initial study evaluation included the following parameters:

a) brittle nails—weak nails that break easily
b) dry nails
c) inability to grow nails longer
d) peeling nails
e) dry or inflamed cuticles.

As reflected in Table V, in the initial evaluation the study subjects had the following complaints:

9 of 12 subjects had brittle nails.

4 of 12 subjects had dry nails.

10 of 12 subjects could not grow their nails longer.

8 of 12 subjects had peeling nails.

5 of 12 subjects had dry or inflamed cuticles.

The initial evaluation parameters were graded according to the following scale:

| | |
|---|---|
| no problem | 0 |
| mild | * |
| moderate | ** |
| severe | *** |

The subjects applied the cream daily for 6 weeks and were then reevaluated. The following factors were evaluated:

a) nail growth rate
b) nail strength and flexibility
c) condition of the cuticle Grading of the reevaluation was done according to the following scale:

| | |
|---|---|
| worse | − |
| same | = |
| better | + |
| much better | ++. |

Results

Table V presents the initial condition and the changes in all the subjects. Table VI shows the changes in the nails and cuticles in the subjects by percentage.

Discussion

The treatment product of the invention had a dramatic effect on both nails and cuticles. All subjects had improvement in either the nail or the cuticle. The treatment product was extremely effective in strengthening the nail and improving the flexibility of the nail. The invention also dramatically increased the rate of nail growth, resulting in longer and stronger nails. An overall improvement in cuticle condition was also observed, including an improvement in inflamed cuticles. None of the subjects had a worsening in any of the parameters evaluated.

The invention was also evaluated on four (4) subjects with nail fungus. Three (3) out of four (4) subjects had an improvement in their condition after six (6) weeks of use.

Conclusion

The composition product of the invention was found to be safe and extremely effective in treating brittle, improved flexibility of the nails and treating dry and peeling nails. The composition of the invention was also found to strengthen nails, improve flexibility, increase the nail growth rate (allowing nails to grow faster and longer), improve the condition of the cuticle, have a beneficial effect on inflamed cuticles, and to decrease the growth of nail fungus (onchio mycosis).

The composition and method of the invention are useful to treat nail fungus by reducing the extent of fungal growth in the presence of the composition of the invention relative to fungal growth in the absence of the composition of the invention. In a preferred embodiment, the nail treatment preparation may also include additional nutrients and vitamins, such as pantothenic acid, biotin, vitamin E, wheat germ protein and others.

TABLE V

NAIL TREATMENT

| SUBJECTS | 1 | 2 | 3 | 4 | 5 | 6 | 7 | 8 | 9 | 10 | 11 | 12 | Ratio |
|---|---|---|---|---|---|---|---|---|---|---|---|---|---|
| Initial Evaluation | | | | | | | | | | | | | |
| Brittle Nails | * | ** | ** | *** | o | * | *** | o | * | *** | o | *** | 9/12 |
| Dry Nails | o | o | o | *** | o | o | *** | o | o | ** | o | * | 4/12 |
| Can't grow long nails | * | *** | *** | ** | *** | *** | o | ** | * | o | ** | ** | 10/12 |
| Peeling nails | * | o | o | o | *** | * | *** | o | * | *** | ** | * | 8/12 |
| Dry, inflamed cuticles | o | o | o | o | ** | o | ** | * | * | o | o | ** | 5/12 |
| Results (at 6 wks) | | | | | | | | | | | | | |
| Nail growth rate | + | + | + | + | ++ | + | + | +++ | + | = | + | ++ | 11/12 |
| Nail strength and flexibility | = | ++ | + | ++ | ++ | + | + | + | + | + | + | + | 11/12 |
| Cuticle condition | + | + | ++ |  | ++ | + | ++ | + | + | ++ | + | + | 11/12 |

Index to Table V:
Initial Evaluation
No problem o
Mild *
Moderate **
Severe ***
Results (at 6 wks)
Worse —
Same =
Better +
Much Better ++
Age range of participants: 22 to 53 years

TABLE VI

Treatment product of the Invention Applied to Nails

| | Worse | Same | Improved |
|---|---|---|---|
| Nail Growth Rate | 0% | 8% | 92% |
| Nail Strength & Flexibility | 0% | 8% | 92% |
| Condition of Cuticles | 0% | 8% | 92% |

Example 9

Chemotherapy Treatment Study

The effect of the composition of the invention was also tested for its ability to reduce or prevent hair fall out in patients undergoing chemotherapy. The composition of Example 1 was tested on three (3) oncological patients. Each patient applied the composition of Example 1 to the scalp every other day.

Subject no. 1 had pancreatic cancer. This subject started applying the composition of Example 1 two weeks prior to chemotherapy no hair fall out was observed after three rounds of chemotherapy.

Subject no 2 had breast cancer. Subject no. 2 started losing hair after the first round of chemotherapy. The subject was administered CAF (cyclophosphoramide, Adriamycin and 5-fluorouracil) during chemotherapy. After the first round of chemotherapy, Subject no. 2 started applying the composition of Example 1 and observed hair regrowth during the course of chemotherapy. The subject did not lose her hair throughout the full course of chemotherapeutic treatment.

Subject no. 3 had Hodjkin's lymphoma. Subject no. 3 started applying the composition of Example 1 after significant hair fall out due to chemotherapy. The subject was submitted to chemotherapy using the MOPP protocol (nitrogen mustard, vincristine, procarbazine, prednisone; Devita V. T., *Cancer, Principles and Practice on Ocology*, 4th Edition, pp. 1836–1845). See also Bonaddona G., *Alternating non-crossed-resistant combination chemotheray with ABVD or MOPP in initial Hodikin's disease*, Ann. Intern. Med., 1986, 104:739–746. Hair regrew during the completion of chemotherapy resulting in a full head of hair at the conclusion of the chemotherapeutic treatment.

The composition and method of the present invention was found to be very effective in strengthening the hair, reducing or preventing hair fall out and regrowing hair in patients undergoing chemotherapy.

Example 10

Hair Transplant Treatment

The effect of the composition of the invention was tested for its ability to condition the scalp, promote faster healing of hair transplant surgical sites, to promote transplanted hair growth, and to reduce or prevent hair transplant fall out.

A plurality of subjects were treated with HAIRPRIME cream immediately after undergoing hair transplant surgery over the course of approximately one year. The results of this study are as follows:

1. In 36.5% of the subjects, the hair transplant grafts did not fall out. This result was very surprising since most hair transplant grafts usually fall out in 100% of subjects undergoing hair transplant surgery.
2. 55% of subjects experienced faster healing of the surgical sites.
3. 20% of subjects reported faster growth of the hair transplants.
4. 77% of the subjects reported less itching than in previous hair transplant surgeries.

The composition and method of the invention has been proven to be very effective in promoting healing, preventing or reducing hair transplant graft fall out, promoting growth of hair transplants and reducing itching.

Thus, there have been described above various methods and products according to the present invention for treating various hair and skin conditions. Modifications in addition to those set forth specifically above are possible within the scope of the present invention which is thus defined only by the following appended claims, which are set forth as further examples of the invention.

What is claimed as new and is desired to be secured by Letters Patent of the United States is:

1. A method for promoting at least one of new hair growth, follicle hair growth, reducing hair loss and remelanizing hair, comprising:

topically applying to a host in need thereof, for an effective period of time, an effective amount of a composition comprising an active agent selected from the group consisting of anole, anethole, fenchone, polymers thereof and mixtures thereof, wherein said active agent is present as a tincture of fennel in a concentration of at least 5% by weight, and wherein there is at least a 50% conversion from vellus to terminal hair and at least 50% of hair remelanization occurs.

2. The method of claim 1 wherein said active agent is present in an amount at least 7.5% by weight.

3. The method of claim 1, wherein said composition comprises anole and anethole.

4. The method of claim 3, wherein said composition further comprises fenchone.

5. The method of claim 1, wherein said host is a female.

6. The method of claim 1, which is a method for promoting growth of eyelash and eyebrow hair.

7. The method of claim 1, which is a method of promoting new hair growth or follicle hair growth.

8. The method of claim 1, which is a method of preventing, stopping or reducing hair loss.

9. The method of claim 1, which is a method of promoting longer and faster hair growth.

* * * * *